United States Patent
Perkins

(10) Patent No.: US 8,282,594 B2
(45) Date of Patent: Oct. 9, 2012

(54) NON-CIRCULAR PORTED PHACOEMULSIFICATION IRRIGATION SLEEVE

(75) Inventor: James T. Perkins, St. Charles, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 2262 days.

(21) Appl. No.: 11/017,586

(22) Filed: Dec. 20, 2004

(65) Prior Publication Data

US 2006/0135975 A1 Jun. 22, 2006

(51) Int. Cl.
*A61B 17/20* (2006.01)
(52) U.S. Cl. .......................... 604/22; 606/169
(58) Field of Classification Search .............. 604/164.01, 604/22, 158, 523, 272–274; 606/129, 169
See application file for complete search history.

(56) References Cited

U.S. PATENT DOCUMENTS

| 4,863,441 | A | * | 9/1989 | Lindsay et al. ............... 604/523 |
| 4,983,160 | A | | 1/1991 | Steppe et al. |
| 5,324,260 | A | * | 6/1994 | O'Neill et al. ............ 604/103.08 |
| 5,725,495 | A | * | 3/1998 | Strukel et al. .................... 604/44 |
| 5,919,157 | A | * | 7/1999 | Strukel ............................ 604/22 |
| 6,007,555 | A | * | 12/1999 | Devine .......................... 606/169 |
| 6,165,190 | A | * | 12/2000 | Nguyen ......................... 606/166 |
| 6,428,501 | B1 | | 8/2002 | Reynard |
| 7,014,629 | B2 | * | 3/2006 | Mackool ....................... 604/274 |
| 2001/0034504 | A1 | | 10/2001 | Zaleski |
| 2004/0153026 | A1 | * | 8/2004 | Mackool ......................... 604/22 |

OTHER PUBLICATIONS

International Search Report (PCT/ISA/210) and Written Opinion (PCT/ISA/237) mailed May 29, 2006.

* cited by examiner

*Primary Examiner* — Theodore Stigell
(74) *Attorney, Agent, or Firm* — Jeffrey B. Powers

(57) ABSTRACT

An ophthalmic phacoemulsification irrigation sleeve 26 includes an elongated resilient tubular body portion 28 having a distal end 30 and a proximal end 32 for surrounding a portion of a shaft of a phacoemulsification needle. An enlarged section 34 is formed on the proximal end 32 for surrounding a hub of a needle and for connection to a phacoemulsification handpiece. Adjacent to the tubular body portion distal end 30 at least one non-circular irrigation port is formed. The shape of the port includes a radiused leading edge closest to the distal end 30 and has tapering, trailing sides 40 resulting in a trailing end 42 having smaller radius than the leading edge radius.

3 Claims, 1 Drawing Sheet

NON-CIRCULAR PORTED PHACOEMULSIFICATION IRRIGATION SLEEVE

BACKGROUND OF THE INVENTION

1. Field of the Invention

The present invention is related to phacoemulsification needles and more specifically, to irrigation sleeves surrounding the needles for use in ophthalmic surgery.

2. Description of Related Art

It is well known to remove cataracts from a patient's eyes, and replace the removed cataract affected lenses with artificial intraocular lenses. It is common and accepted practice to remove the cataract affected lenses via phacoemulsification.

Phacoemulsification enables a lens to be removed from the eye through a small incision, typically on the order of 3 mm. Phacoemulsification involves using high frequency ultrasonic energy transmitted through a handpiece into a phacoemulsification needle to fragment the affected lens. Once the lens is fragmented or emulsified, the lens material is aspirated, along with irrigation fluid through a lumen of the phacoemulsification needle, and through the handpiece and into a collection reservoir of a surgical system.

During aspiration of the lens material, it is typical to simultaneously insert a flow of irrigation fluid into the eye. This flow is provided to prevent the eye from collapsing during aspiration and to prevent serious damage to the eye from such collapse. It is also typical that a phacoemulsification needle provides what is commonly referred to as coaxial irrigation. This coaxial irrigation provides the flow of irrigation fluid into the eye via a resilient sleeve surrounding the needle. The irrigation sleeve typically includes circular irrigation ports adjacent to the distal end of the sleeve so that fluid flows from the handpiece in between the sleeve and the outside of the needle and through the circular ports. While phacoemulsification and coaxial irrigation have proven to be very successful and safe, there are some drawbacks, which may be improved upon.

One such drawback is that because of the prior art's circular shaped irrigation ports, when the irrigation sleeve becomes compressed upon insertion into an incision in the eye, the trailing edge of the circular port tends to flare-out and therefore, increase the cross-sectional area or footprint that must be inserted past the incision in the eye. This flaring of the trailing edge tends to cause the sleeve to bunch-up and not be properly inserted into the eye, particularly into a tight wound. A tight wound or a small incision is often preferred to minimize the damage to the eye, and to also provide a maximum amount of sealing around the sleeve of the needle to prevent loss of fluids from the surgical site.

Therefore, it would be desirable to have an irrigation sleeve with a port shape, which would not have a flaring trailing edge and therefore, be easier to insert into an eye's incision.

DETAILED DESCRIPTION OF THE PREFERRED EMBODIMENT

Figure 1:
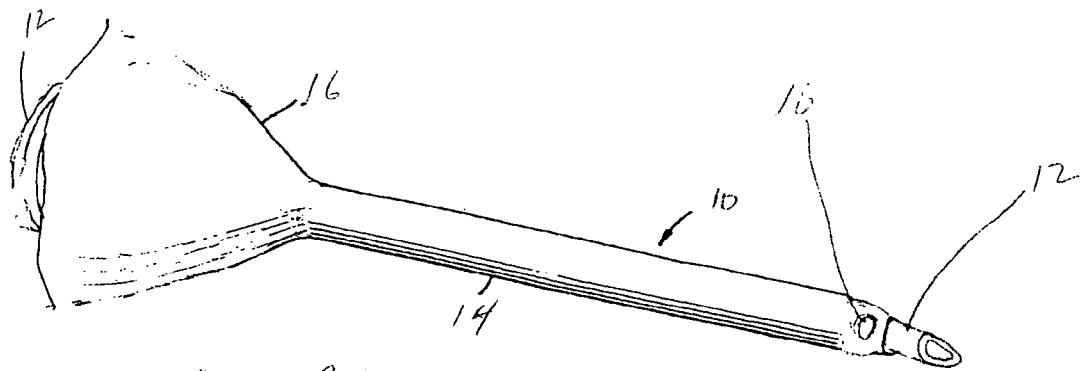
FIG. 1 is a perspective view of a prior art phacoemulsification irrigation sleeve with a circular port attached over a needle.

FIG. 1 shows a prior art phacoemulsification irrigation sleeve 10 surrounding a phaco needle 12. Sleeve 10 includes a generally tubular body portion 14 and an enlarged section 16 formed on a proximal end, as shown. In use, enlarged section 16 is attached to a phacoemulsification handpiece for use during surgery. The phacoemulsification handpiece is not shown. The sleeve 10 includes the prior art circular ports 18 for irrigation.

Figure 2:
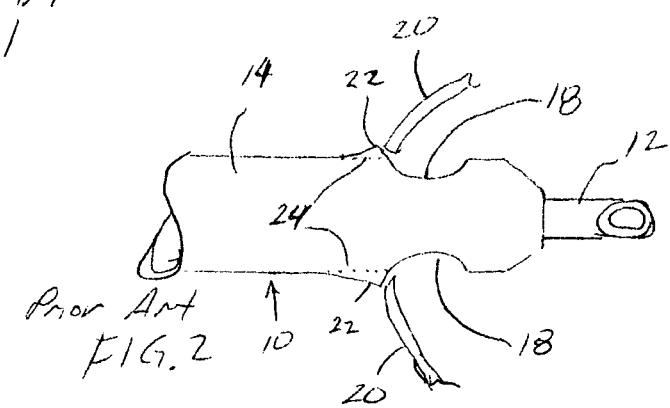
FIG. 2 is a prior art partial top-view of a circular port sleeve which has been compressed and illustrating the flared trailing edge.

While the prior art sleeve 10 works satisfactorily and produces good results, it has a drawback that is illustrated in FIG. 2. FIG. 2 shows the irrigation sleeve 10 being inserted into an eye 20, as the incision in the eye 20 compresses tubular body portion 14. Flared portions 22 of the trailing edge of port 18 can cause the sleeve 10 to bunch-up as the sleeve 10 and needle 12 are being inserted into the eye 20. Dotted lines 24 show the position of tubular body portion 14, in its uncompressed position. It is believed that all prior art irrigation ports have been circular in shape, which results in the flaring shown at 22. It would be highly desirable to have an irrigation port which did not flare and therefore, would reduce the likelihood of the sleeve bunching upon insertion into an eye during surgery.

Figure 3:
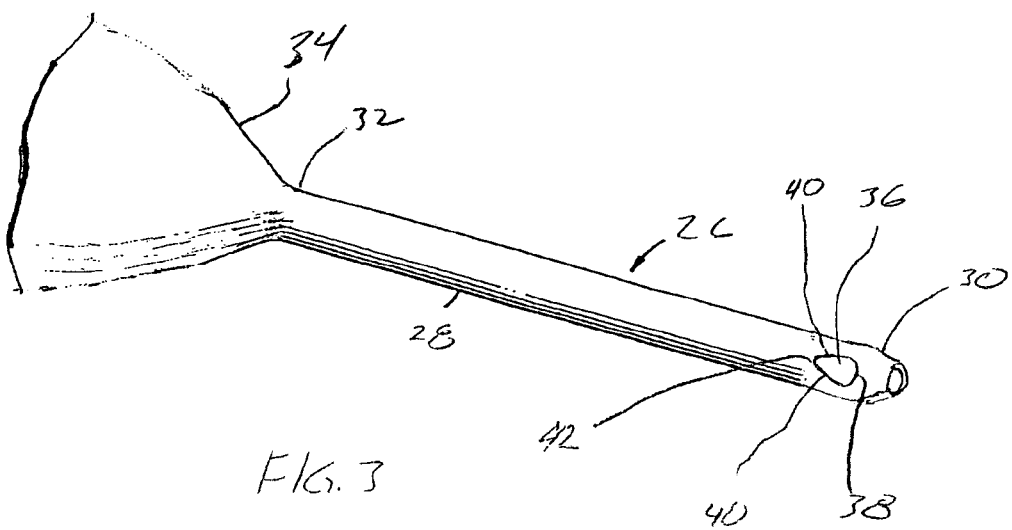
FIG. 3 is a partial perspective view of a phacoemulsification irrigation sleeve in accordance with the present invention.

FIG. 3 is a partial perspective view of an irrigation sleeve 26 in accordance with the present invention. Sleeve 26 includes an elongated resilient tubular body portion 28 having a distal end 30 and a proximal end 32 for surrounding a portion of a shaft of a phacoemulsification needle (not shown). Sleeve 26 is preferably formed of silicone or other suitable compliant material for use in ophthalmic surgery. An enlarged section 34 is formed on the proximal end 32 of the body portion 28 for surrounding a hub of a needle (not shown) and for connection to a phacoemulsification handpiece (not shown). Adjacent to the tubular body portion distal end 30, preferably at least one non-circular irrigation port 36 is formed. The shape of the port 36 includes a radiused leading edge 38 closest to the distal end 30 and has tapering trailing sides 40 resulting in a trailing end 42 having a smaller radius than the leading edge radius 38. Though irrigation port 36 shown is generally teardrop in shape, other shapes which essentially have an elongated opening with tapering sides, that is sides that get smaller from the leading edge to the trailing edge, may fall within the scope of the present invention. It is noted that port 36 preferably has a larger cross-sectional area that a circular port with a radius equal to that of leading edge 38. This larger cross-sectional area allows for an increase in irrigation flow compared to the circular port.

Figure 4:
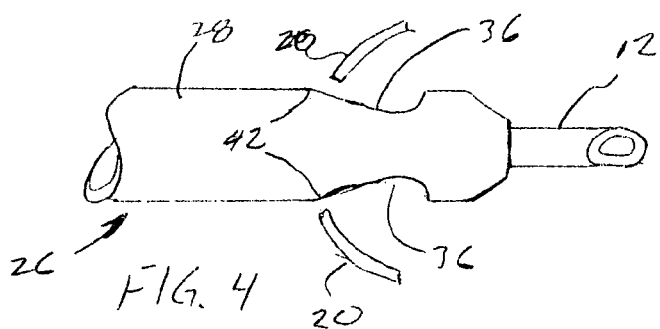
FIG. 4 is a partial top-view of an irrigation sleeve inserted onto a phacoemulsification needle illustrating the lack of flaring of a trailing edge.

FIG. 4 shows a partial top elevation view of inventive sleeve 26 inserted onto a needle 12 and being inserted into an eye 20. It can be seen that because of the elongated, narrowing or tapering non-circular shape of the irrigation port 36, no bunching or flaring occurs at trailing edge 42. This non-circular, elongated shape allows the sleeve 26 to be more easily inserted into the eye and prevent bunching of the body portion 28 as compared to that described above with respect to the circular irrigation port of the prior art in FIG. 2.

I claim:

1. An ophthalmic phacoemulsification irrigation sleeve comprising:

an elongated resilient essentially tubular body portion having a distal end and a proximal end for surrounding a portion of a shaft of a phacoemulsification needle;
an enlarged section formed on the proximal end of the body portion for surrounding a hub of a needle and for connection to a phacoemulsification handpiece; and
wherein adjacent to the tubular body portion distal end at least one non-circular irrigation port is formed such that a shape of the port includes a radiused leading edge closest to the distal end and has tapering trailing sides resulting in a trailing end having a smaller radius than the leading edge radius.

2. The sleeve of claim 1, wherein the sleeve is formed of silicone.

3. An ophthalmic phacoemulsification irrigation sleeve and needle comprising:

a phacoemulsification irrigation sleeve including;
an elongated resilient essentially tubular body portion having a distal end and a proximal end for surrounding a portion of a shaft of a phacoemulsification needle;
an enlarged section formed on the proximal end of the body portion for surrounding a hub of a needle and for connection to a phacoemulsification handpiece; and
wherein adjacent to the tubular body portion distal end at least one non-circular irrigation port is formed such that a shape of the port includes a radiused leading edge closest to the distal end and has tapering trailing sides resulting in a trailing end having a smaller radius than the leading edge radius; and
a phacoemulsification needle at least partially surrounded by the sleeve.

* * * * *